United States Patent

Omura et al.

[11] Patent Number: 6,139,851
[45] Date of Patent: Oct. 31, 2000

[54] HAIR COSMETICS

[75] Inventors: Takayuki Omura; Ayumi Kimura; Yasunari Nakama, all of Yokohama, Japan

[73] Assignee: Shiseido Company, Ltd., Tokyo, Japan

[21] Appl. No.: 09/046,616

[22] Filed: Mar. 24, 1998

[30] Foreign Application Priority Data

Mar. 24, 1997 [JP] Japan .................................. 9-088768

[51] Int. Cl.⁷ .............................. A61K 6/00; A61K 7/00; A61K 7/06
[52] U.S. Cl. ...................... 424/401; 424/70.1; 424/70.11; 424/70.12; 514/937
[58] Field of Search .................................. 424/70.1, 401, 424/70.11, 70.12; 514/937

[56] References Cited

U.S. PATENT DOCUMENTS 4,839,167  6/1989  Yamamoto et al. ....................... 424/71
5,660,819  8/1997  Tsubaki et al. ......................... 424/70.1

FOREIGN PATENT DOCUMENTS 0535367    4/1993  European Pat. Off. ......... A61K 7/06
0914814A1  5/1999  European Pat. Off. ......... A61K 7/00

OTHER PUBLICATIONS

Patent Abstracts of Japan & JP 08 073313 A (Shiseido Co., Ltd.)
Patent Abstracts of Japan & JP 02 167212 A (Shisedo Co., Ltd.)
Patent Abstracts of Japan & JP 06 100413 A (Kanebo, Ltd.)

*Primary Examiner*—Thurman K. Page
*Assistant Examiner*—S. Howard
*Attorney, Agent, or Firm*—Townsend & Banta

[57] ABSTRACT

A lower alcohol-in-oil type emulsified hair cosmetic which contains one or more types of silicone derivatives, one or more types of specific polyether modified silicone and a lower alcohol. The emulsified hair cosmetic with very good stability by using for the emulsifier a polyether modified silicone without using a surfactant or organic modified clay mineral for the emulsifier.

6 Claims, No Drawings

HAIR COSMETICS

RELATED APPLICATION

This application claims the priority of Japanese Patent application No.9-88768 filed on Mar. 24, 1997, which is incorporeted herein by reference.

BACKGROUND OF THE INVENTION

1. Field of the Invention

This invention relates in general to a lower alcohol in-oil type emulsified hair cosmetic, and more particularly to a lower alcohol-in oil type emulsified hair cosmetic which has extremely good emulsification stability, good application ease and a split ends mending effect.

2. The Prior Art

Silicone derivatives in the form of silicone oil are known to have superior water repellency, heat resistance and oxidation resistance and are frequently used in various industrial materials. In particular, they spread lightly and have a refreshing texture when used for cosmetic materials or quasi-drug materials and therefore they are used in various applications including makeup cosmetics and hair cosmetics.

However, silicone oil has a shortcoming in that it is hard to incorporate it into a stable water-in-oil type emulsified composition and a solution for this problem has been desired. To solve this shortcoming, an emulsified composition comprising water, polyhydric alcohol and an oil phase which contains polyoxyalkylene modified organopolysiloxane, water swelling clay minerals, a quarternary ammonium salt type cation surfactant and silicone oil was proposed. Even this emulsified composition, however, was not adequate in terms of long term stability.

On the other hand, for the purpose of coating split ends, dimethyl silicone gum, polyvinylpyrolidone-type polymer, acrylic acid type polymer, polysaccharide, polypeptides, etc. have been blended in hair cosmetics. Recently, it was reported that a hair cosmetic using both a type of polysiloxane-oxyalkylene copolymer and a silicone derivative had a good tactile sense and was superior in adhering split portions of hair (Japanese unexamined patent publication Tokkai Hei 6-157247).

However, with these methods, even though they had a good tactile sense, the effect could not be reproduced once peeling occurred and there were many problems regarding the tactile sense such as creaking, dryness and stiffness. Furthermore, there were problems in terms of appearance such as flaking.

BRIEF SUMMARY OF THE INVENTION

The inventors conducted earnest investigation in view of the aforementioned problems and discovered that a stable lower alcohol-in-oil type emulsified composition whose oil phase contained a silicone derivative in the form of silicone oil could be obtained by adding for an emulsifier a polyether modified silicone with a specific polyoxyalkylene group content, and that the obtained cream-like emulsion had a unique application ease including spreading lightly, drying quickly and exhibiting no stickiness and also was superior in terms of sustained gloss of the hair and adhesion of split portions of hair, thus completing the present invention.

The present invention provides a lower alcohol-in-oil type emulsified hair cosmetic which contains; (A) one or more types of silicone derivative; (B) one or more types of poly ether modified silicone represented by the following general formula (1):

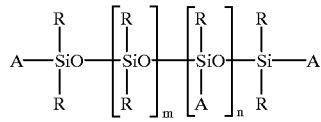

and (C) a lower alcohol.

In this formula, A denotes a group selected from among a methyl group, a phenyl group and a polyoxyalkylene group represented by the general formula $-C_3H_6O(C_2H_4O)_a(C_3H_6O)_bR'$ (where R' denotes a group selected from among a hydrogen atom, acyl group and alkyl group with a carbon number of 1–4, a denotes an integer 5–50 and b denotes an integer 5–50), and at least one of the three A's is a polyoxyalkylene group. R denotes a methyl group or phenyl group, m denotes an integer 50–1,000 and n denotes an integer 1–40. The polyether modified silicone contains 40 wt % or more of polyoxyalkylene groups in its molecules and the molecular weight of the polyether modified silicone is 30,000 or more.

The present invention invention also provides the aforementioned lower alcohol-in-oil type emulsified hair cosmetic wherein said silicone derivative is a high molecular weight dimethylpolysiloxane represented by the following general formula (2).

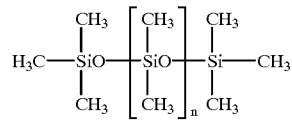

In this formula, n denotes an integer 3,000 20,000.

The present invention invention also provides the aforementioned lower alcohol in-oil type emulsified hair cosmetic wherein said silicone derivative is an amino modified or ammonium modified silicone represented by the following general formula (3):

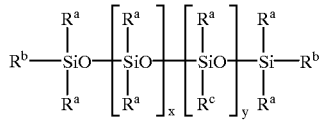

In this formula, $R^a$ denotes a methyl group or a phenyl group, and $R^b$ denotes the same as $R^c$ or a methyl group or hydroxyl group. $R^c$ denotes a substitutional group containing an amino group or ammonium group represented by the formula $R^dZ$ {$R^d$ denotes a divalent alkylene group containing 3–6 carbon atoms, Z denotes a monovalent group selected from among $-NR^e_2$, $-N^+R^e_3A^-$, $-NR^e(CH_2)_nNR^e_n$, $NR^e(CH_2)_nN^+R^e_3A^-$ and $-NR^e(CH_2)_nN(R^e)CO(R^F)$ ($R^e$ denotes hydrogen or an alkyl group containing 1–4 carbon atoms, $R^F$ denotes an alkyl group containing 1–4 carbon atoms, A denotes a chlorine atom, bromine atom or iodine atom, and n denotes an integer 2–6.)}, x and y each denotes a positive integer, x+y denotes an integer 3,000–20,000 and y/x is in the range of 1/500–1/10,000.

The present invention invention also provides the aforementioned lower alcohol-in-oil type emulsified hair cosmetic wherein the content of said lower alcohol is 30–80 wt % of the total emulsified hair cosmetic.

DETAILED DESCRIPTION OF THE INVENTION

The configuration of the present invention is described in detail below.

The polyether modified silicone used for the emulsifier in the present invention is organopolysiloxane containing polyoxyalkylene groups represented by the aforementioned general formula (1). In the present invention, a commercial product (TS Polymer 50-IP from Toray Dow-Corning Silicone Co., Ltd.) can be used. The primary point of the present invention is that it can provide a lower alcohol-in-oil type emulsified hair cosmetic with very good emulsion stability by using for the emulsifier a specific polyether modified silicone represented by the aforementioned general formula (1) (lower alcohol-in-oil type emulsified hair cosmetics using oil containing silicone oil for the continuous phase has a problem in emulsification stability when conventional surfactants are used). In the present invention, there is no need to use a conventional surfactant for the emulsifier.

At least one of the three A's in the aforementioned general formula (1) of the polyether modified silicone has to be a polyoxyalkylene group represented by the general formula $—C_3H_6O(C_2H_4O)_a(C_3H_6O)_bR'$ and 40 wt % or more of polyoxyalkylene groups has to be contained in the polyether modified silicone molecules. Specific examples of the acyl group for R' in the polyoxyalkylene group include a formyl group, acetyl group, propionyl group, butyroyl group, acryloyl group, benzoyl group and toluoyl group, and specific examples of the alkyl group with a carbon number of 1–4 include a methyl group, ethyl group, i-propyl group, n-propyl group, t-butyl group and n-butyl group. In the polyoxyalkylene group, if a or b is less than 5, then the polyether modified silicone will not exhibit a sufficient emulsifying effect. If a or b is more than 50, then the obtained emulsified hair cosmetic will be sticky. The polyoxyalkylene group content is 40 wt % or more, and preferably in the range of 40–70 wt %. This is because the emusifying ability on nonpolar oil other than silicone oil decreases when the polyoxyalkylene group content is less than 40 wt %, and the obtained emulsified hair cosmetic becomes sticky when it is more than 70 wt %. m is an integer 50–1,000 and preferably an integer 15014 1,000. n is an integer 1–40. This is because the emulsifying effect is not sufficient if m is less than 50 and n is less than 1, and the obtained emulsified hair cosmetic becomes sticky if m is more than 1,000 and n is more than 40. The ratio m:n is preferably in the range between 200:1 and 5:1, and more preferably 60:1–15:1.

For the polyether modified silicone, those for which every R in the aforementioned general formula (1) is a methyl group are preferable.

The molecular weight of the polyether modified silicone is 30,000 or more, and preferably 50,000 or more. This is because the emulsifying ability of silicone derivatives decreases when the molecular weight of the polyether modified silicone is less than 30,000.

The viscosity of the polyether modified silicone is not limited in particular, but it is desirable that the viscosity of a 50 wt % solution of the polyether modified silicone in octamethylsiloxane or isoparaffin is in the range of 1,000–100,000 cps for the sake of formation of a stable emulsion and smooth feeling.

The content of the polyether modified silicone is not limited in particular, but a preferable range is 1–50 wt % of the total emulsified hair cosmetic and a more preferable range is 3–30 wt %. If the content of the polyether modified silicone is less than 1 wt %, then stable emulsification becomes difficult and if it is more than 50 wt % then the emulsified hair cosmetic will be sticky.

In the present invention, a lower alcohol-in-oil type (hereafter referred to as simply "alcohol-in-oil type" or "A/O type" as well) emulsified hair cosmetic means that the discontinuous phase is a lower alcohol or a mixed solution of water and a lower alcohol.

The type of the lower alcohol used in the present invention (hereafter referred to as simply "alcohol" as well) is not limited in particular, but methanol or ethanol is preferable. Considering safety, ethanol is particularly preferable. When using i-propanol, n-propanol, t- butanol, s-butanol, etc., they should be used with ethyl alcohol because they are too hydrophobic and are therefore hard to emulsify.

While it was difficult to obtain a stable water-in-oil type emulsified composition with a high alcohol concentration, the present invention makes it possible to obtain a stable emulsified composition even when the alcohol content in the emulsified composition is 30 wt % or more. This fact illustrates the importance of the present invention.

The content of the alcohol used in the present invention is preferably 6–80 wt % of the total emulsified hair cosmetic, and more preferably in the range of 10–80 wt %. In particular, a characteristic of the present invention is the fact that the emulsification stability is high even with a high alcohol concentration where the alcohol content is 30–80 wt %. If the alcohol content is less than 6 wt %, then oil separation may occur over time and emulsification stability deteriorates. If it is more than 80 wt % then alcohol separates from the emulsified hair cosmetic and a stable emulsified composition may not be obtained.

The present invention includes cases where the lower alcohol phase, which is the discontinuous phase, is a mixed solution with water. In these cases, the weight ratio of the lower alcohol to water should preferably be ⅕ or more. If the ratio of the lower alcohol to water is less than ⅕ then the polyether modified silicone may cause gelation of the whole system to increase the viscosity excessively and the emulsification becomes difficult.

The silicon derivative used in the present invention is organo polysiloxanes containing a siloxane bond(s) including dimethyl polysiloxane, methylphenyl polysiloxane, polyether modified silicone, epoxy modified silicone, fluorine modified silicone, alcohol modified silicone, alkyl modified silicone, alkoxy modified silicone and organic silicone resin. The silicon derivative constitutes the oil phase, which is the continuous phase in the emulsified hair cosmetic of the present invention. For the silicone derivative, those represented by the aforementioned general formula (2) or (3) is preferable. Also, those represented by the following general formulas (4)–(17) with a general formula of $R_nSiO_{(4-n)/2}$ are preferably used as well. The polyether modified silicone represented by the aforementioned general formula (1) which is used for the emulsifying agent is also a silicone derivative as defined in the present invention, and if the amount of it is sufficient to form the oil phase then other silicone derivatives do not have to be contained.

(1) Dimethyl polysiloxane

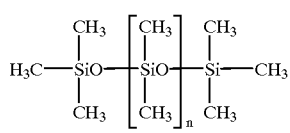
(4)

In this formula, n denotes an integer 3–20,000.

(2) Methylphenyl polysiloxane

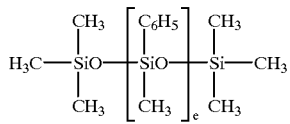
(5)

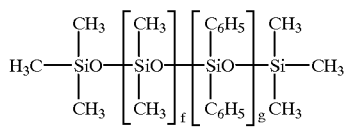
(6)

e denotes an integer 1–20,000 and f+g denotes an integer 1–500.

(3) Polyether modified silicone

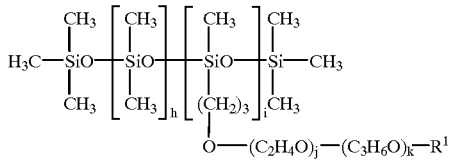
(7)

$R^1$ denotes a hydrogen atom or an alkyl group with a carbon number of 1–12, h denotes an integer 1–100 (preferably 3–30), i denotes an integer 1–50 (preferably 1–30), j denotes an integer 1–50 (preferably 3–30), k denotes an integer 0–50 (preferably 0–30). The total of h and i is an integer of 15 or larger, and the total of j and k is an integer of 5 or larger.

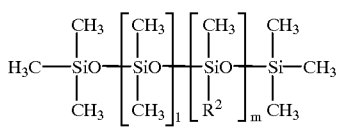
(8)

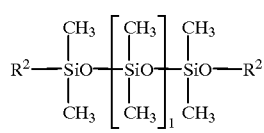
(9)

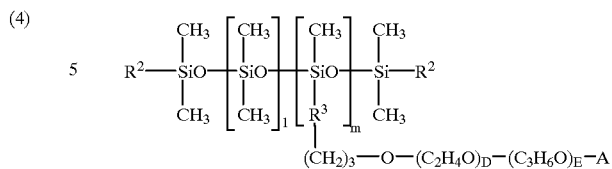
(10)

l denotes a number 1–2,000 and m denotes a number 1–1,000. $R^2$ denotes a methyl group or phenyl group, $R^3$ denotes an alkylene group with a carbon number of 1–3. A denotes a hydrogen atom or an alkyl group with a carbon number of 1–12. D and E each denotes an integer 0–50, and D+E≧1.

(4) Epoxy modified silicone

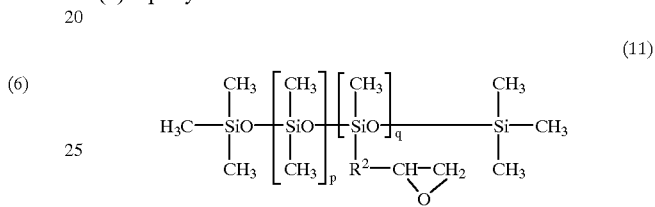
(11)

p denotes an integer 1–500 (preferably 1–250), q denotes an integer 1–50 (preferably 1–30) and $R^3$ denotes an alkylene group with a carbon number of 1–3.

(5) Fluorine modified silicone

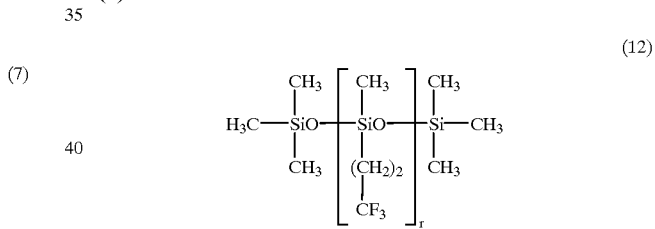
(12)

r denotes an integer 1–400 (preferably 1–250).

(6) Alcohol modified silicone

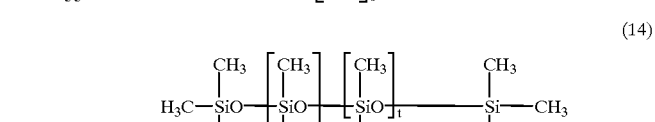
(13)

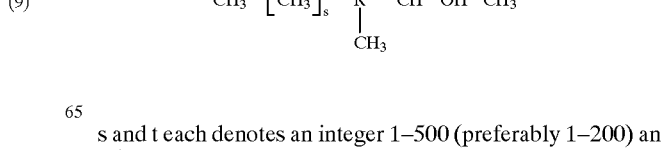
(14)

s and t each denotes an integer 1–500 (preferably 1–200) and $R^4$ denotes $C_FH_{2F}$ (F denotes an integer 0–4).

(7) Alkyl modified silicone

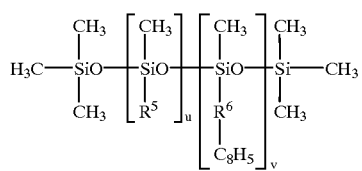

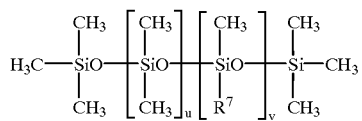

u and v each denotes an integer 1–500 (preferably 1–200). $R^5$ denotes an alkyl group with a carbon number of 2–18, $R^6$ denotes $C_GH_{2G}$ (G denotes an integer 0–4 ) and $R^7$ denotes an alkyl group with a carbon number of 10–16.

(8) Alkoxy modified silicone

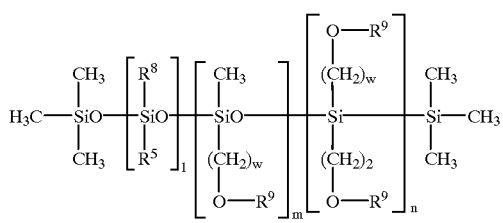

$R^6$ denotes a methyl group and phenyl group, $R^0$ denotes an alkyl group with a carbon number of 1–28 (preferably 12–22), w denotes an integer 0–6, l denotes an integer 1–3,000 and m and n denote integers for which m+n=1–500.

(9) Organic silicone resin

General formula: $R_nSiO_{(4-n)/2}$ It comprises an appropriate combination of $R_3SiO_{1/2}$ units, $R_2SiO$ unites, $RSiO_{3/2}$ unites and $SiO_{1/2}$ units. The ratio is such that the average unit is represented by the general formula $R_nSiO_{(4-n)/2}$ (where R denotes a hydrocarbon group with a carbon number of 1–6 or phenyl group and n denotes a value of 1.0–1.8).

In the present invention, one or more types of silicon derivative form the oil phase. The oil phase may contain oil components other than the silicon derivative. Depending on the purpose, oil components listed below including hydrocarbon oils, higher fatty acids, higher alcohols, synthetic ester oils, liquid oils/fats, solid oils fats and waxes can be blended in.

Examples of the hydrocarbon oils include liquid paraffin, ozokerite, squalene, pristane, paraffin, ceresin, squalene, vaseline and microcrystalline wax.

Examples of the higher fatty acids include lauric acid, myristic acid, palmitic acid, stearic acid, behenic acid, oleic acid, 12-hydroxystearic acid, undecylenic acid, toll oil, isostearic acid, linoleic acid, linolenic acid, eicosapentaenoic acid (EPA) and docosahexaenoic acid (DHA).

Examples of the higher alcohols include linear chain alcohols such as lauryl alcohol, cetyl alcohol, stearyl alcohol, behenyl alcohol, myristyl alcohol, oleyl alcohol and cetostearyl alcohol as well as branched chain alcohols such as monostearyl glycerine ether (batyl alcohol), 2-decyltetradecinol, lanolin alcohol, cholesterol, phytosterol, hexyldodecanol, isostearyl alcohol and octyl dodecanol.

Examples of the synthetic ester oils include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid ester, N-alkyl glycol monoisostearate, neopentyl glycol dicaprate, diisostearyl malate, glyceryl di-2-heptylundecanoate, trimethylolpropane tri-2- ethylhexylate, trimethylolpropane triisostearate, pentaneerythritol tetra-2-ethylhexylate, glyceryl tri-2-ethylhexylate, trimethylolpropane triisostearate, cetyl 2-ethylhexanoate, 2-ethylhexyl palmitate, glyceryl trimyristate, tri-2-heptylundecanoic glyceride, castor oil fatty acid methyl ester, oleyl oleate, cetostearyl alcohol, acetoglyceride, 2-heptylundecyl palmitate, diisopropyl adipate, N-lauroyl-L-glutamic acid-2-octyldodecyl ester, di-2-heptylundecyl adipate, ethyl laurate, di-2-ethylhexyl cebatate. 2-hexyldecyl myristate, 2-hexyldecyl palmitate, 2-hexyldecyl adipate, diisopropyl cebatate, 2-ethylhexyl succinate, ethyl acetate, butyl acetate, amyl acetate and triethyl ||̣ trate.

Examples of liquid oils/fats include avocado oil, tsubaki oil, turtle oil, macadamia nut oil, corn oil, mink oil, olive oil, rape seed oil, egg yolk oil, sesame seed oil, persic oil, wheat germ oil, sasanqua oil, castor oil, linseed oil, safflower oil, cotton seed oil, perilla oil, soybean oil, peanut oil, tea seed oil, kaya oil, rice bran oil, chinese wood oil, Japanese wood oil, jojoba oil, germ oil, triglycerol, glyceryl trioctanoate and glyceryl triisopalmitate.

Examples of the solid oils/fats include cacao butter, coconut oil, horse tallow, hardened coconut oil, palm oil, beef tallow, sheep tallow, hardened beef tallow, palm kernel oil, pork tallow, beef bone tallow, Japanese core wax, hardened oil, neatsfoot tallow, Japanese wax and hydrogenated castor oil.

Examples of the waxes include honeybee wax, candelilla wax, cotton wax, carnauba wax, bayberry wax, tree wax, whale wax, montan wax, bran wax, lanolin, kapok wax, lanolin acetate, liquid lanolin, sugar cane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol and POE hydrogenated lanolin alcohol ether.

In the present invention, the silicone derivative content should preferably be 1–85 wt %, more preferably 3–70 wt %, of the total emulsified hair cosmetic. This content is the total amount including the polyether modified silicone represented by the general formula (1) which is used as the aforementioned emulsifying agent. When oil components other than the silicone derivative are blended in, the total of the silicone derivative and other oil which form the oil phase should preferably be 5–90 wt % of the total emulsified hair cosmetic.

In addition to the aforementioned essential ingredients, depending on the purpose, other ingredients which are usually blended into cosmetics can be blended in as necessary within the quantitative and qualitative range which does not affect the effect of the present invention. Examples of these ingredients include water soluble polyhydric alcohols such as ethylene glycol, propylene glycol, 1,3 butylene glycol, glycerine, sorbitol and polyethylene glycol, humectants such as hyaluronic acid, chondroitin sulfuric acid and pyrolidonecarboxylate, ultraviolet light absorbents, ultraviolet light scattering agents, resins such as acrylic type resins and polyvinylpyrolidone, proteins or decomposed proteins such as soybean protein, gelatin, collagen, silk fibroin and elastin, preservatives such as ethyl paraben and butyl paraben, various amino acids, activating agents such as biotin and pantothenic acid, blood flow promoting agents such as τ-oryzanol, sodium dextran sulfate, vitamin E derivatives and nicotine derivatives, anti-seborrhea agents such as sulfur and thiantol, thickeners such as carboxyvinyl polymer, drugs, perfumes and coloring agents.

The water-in-oil and/or alcohol-in-oil type emulsified hair cosmetic of the present invention can be used as various hair cosmetics including general hairdressings, split ends coating agents, shampoos, rinse agents, treatment agents, setting agents, permanent wave liquid and mascara.

According to the present invention, a lower alcohol-in-oil type emulsified hair cosmetic with very good emulsification stability which uses a silicon derivative for the oil phase can be obtained. The emulsified hair cosmetic of the present invention gives excellent gloss and smooth tactile sense to the hair, has an excellent application ease because it spreads easily and is not sticky, and it can also adhere and mend split ends.

EXAMPLES

Further details of the present invention are described below by referring to examples. The present invention is not limited to these examples. The units of the blended amounts are weight percent.

First, the emulsification stability of the lower alcohol-in-oil type emulsified hair cosmetic of the present invention with a high alcohol concentration was investigated in comparison with the following conventional typical water-in-oil type emulsified hair cosmetic.

(Comparative example 1)

|      |                                                                   | (wt%) |
|------|-------------------------------------------------------------------|-------|
| (1)  | Isoparaffin                                                       | 15.0  |
| (2)  | Dimethyl polysiloxane (n = 3,000 in the general formula (2))      | 10.0  |
| (3)  | Distearyldimethyl ammonium chloride                               | 0.8   |
| (4)  | Diglyceryl diisostearate                                          | 2.0   |
| (5)  | Dextrin fatty acid ester                                          | 1.2   |
| (6)  | Hectorite treated withe dimethylstearylammonium chlorid           | 1.5   |
| (7)  | Ion exchanged water                                               | 30.0  |
| (8)  | Ethanol                                                           | 35.0  |
| (9)  | Glycerine                                                         | 4.0   |
| (10) | Polyethylene glycol 6000                                          | 0.5   |

(Preparation method)

The components (1)–(6) were heated up to 70° C. and mixed and dissolved to prepare the oil phase. The components (7)–(10) were then dispersed and mixed at 70° C. and gradually added to the oil phase using a disper for agitation. After a thorough and homogeneous mixing and agitation, the system was cooled to obtain the target alcohol-in-oil type emulsified hair cosmetic with a viscosity of 65,000 cps.

(Comparative example 2)

|     |                                                              | (wt%) |
|-----|--------------------------------------------------------------|-------|
| (1) | Isoparaffin                                                  | 15.0  |
| (2) | Dimethyl polysiloxane (n = 3,000 in the general formula (2)) | 10.0  |

(Comparative example 2) -continued

|     |                                                                                   | (wt%) |
|-----|-----------------------------------------------------------------------------------|-------|
| (3) | Polyether modified silicone (m = 35, n = 7, a = 20 and b = 0 in the general formula (18)) | 10.0  |
| (4) | Ion exchanged water                                                               | 25.0  |
| (5) | Ethanol                                                                           | 35.0  |
| (6) | Glycerine                                                                         | 4.0   |
| (7) | Sodium glutamate                                                                  | 0.5   |
| (8) | Polyethylene glycol 6000                                                          | 0.5   |

(Preparation method)

An alcohol-in-oil type emulsified hair cosmetic was obtained in the same manner as in Comparative example 1.

(Example 1)

|     |                                                                                                        | (wt%) |
|-----|--------------------------------------------------------------------------------------------------------|-------|
| (1) | Isoparaffin                                                                                            | 15.0  |
| (2) | Dimethyl polysiloxane (n = 3,000 in the general formula (2))                                           | 10.0  |
| (3) | Polyether modified silicone (50% solution of the general formula (18) with m = 400, n = 10, a = 19 and b = 19 in isoparaffin) | 10.0  |
| (4) | Ion exchanged water                                                                                    | 25.0  |
| (5) | Ethanol                                                                                                | 35.0  |
| (6) | Glycerine                                                                                              | 4.0   |
| (7) | Sodium glutamate                                                                                       | 0.5   |
| (8) | Polyethylene glycol 6000                                                                               | 0.5   |

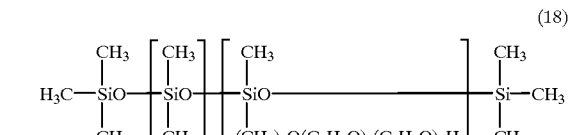

(18)

(Preparation method)

The components (1)–(3) were mixed at room temperature to prepare the oil phase. The components (4)–(8) were then mixed and agitated and gradually added to the oil phase using a disper for agitation. After a thorough agitation, the target alcohol-in-oil type emulsified hair cosmetic with a viscosity of 50,000 cps was obtained.

The results of the emulsification stability are shown in Table 1.

TABLE 1

| | Emulsification stability |
|---|---|
| Comparative example 1 | Demulsification occurred after a week at room temperature. |
| Comparative example 2 | Creaming occurred after a month at room temperature. |
| Example 1 | Stable with no changes after three months at 50° C. |

Table 1 indicates that Comparative examples 1 and 2 did not produce a stable alcohol-in-oil type emulsified hair cosmetic with a high alcohol concentration but that Example 1 of the present invention produced a very stable alcohol-in-oil type emulsified hair cosmetic with a high alcohol concentration.

The emulsification stability was investigated by comparing the polyether modified silicone used in the present invention and other polyether modified silicones when they were used in alcohol-in-oil type emulsified hair cosmetics with a high alcohol concentration.

Tables 3 to 5 show the emulsification stability and stickiness for various combinations of a, b, m and n of the polyether modified silicone represented by the general formula (18) used in emulsified hair cosmetics with the basic recipe shown in Table 2.

TABLE 2

| Basic recipe | Weight (%) |
|---|---|
| (1) Dimethyl polysiloxane 6CS | 15.0 |
| (2) Dimethyl polysiloxane (n = 3,000 in the general formula (2)) | 15.0 |
| (3) Polyether modified silicone (50% solution of the general formula (18) in isoparaffin) | 10.0 |
| (4) Sodium glutamate | 1.0 |
| (5) Polyethylene glycol 6000 | 1.0 |
| (6) Ion exchanged water | 23.0 |
| (7) Ethanol | 35.0 |

(Preparation method)

The components (1), (2) and (3) were mixed together and then the components (4), (5), (6) and (7) were gradually added to this mixture while agitation with a disper was carried out to emulsify it.

The judgment criteria of emulsification stability and stickiness in each table are as follows.

"Emulsification stability"

⊚: Stable with no changes after three months at 50° C.
○: Stable with no changes after one month at 50° C.
Δ: Stable with no changes after two weeks at 50° C.
X: Separated within one week at 50° C.

"Stickiness"

○: Eight or more members of a specialist panel of ten women judged the sample to be not sticky and having a good usability.
Δ: Eight or more members of a specialist panel of ten women judged the sample to be slightly sticky.
X: Eight or more members of a specialist panel of ten women judged the sample to be sticky.

Table 3 shows the results of testing the emulsification stability and stickiness with various values of a and fixed values of m=400. n=10 and b=20 in the basic recipe shown in Table 2.

TABLE 3

| | | Comparative example 3 | Example 2 | Example 3 | Example 4 | Comparative example 4 |
|---|---|---|---|---|---|---|
| Polyether | m | 400 | 400 | 400 | 400 | 400 |
| modified | n | 10 | 10 | 10 | 10 | 10 |
| silicone | a | 3 | 5 | 20 | 47 | 60 |
| (the general formula (2)) | b | 20 | 20 | 20 | 20 | 20 |
| Emulsification stability | | x | ⊚ | ⊚ | ⊚ | ⊚ |
| Stickiness | | ○ | ○ | ○ | ○ | Δ |

Table 3 indicates the following: when a is 3, the emulsification stability is poor; when a is from 5 to approximately 50 both the emulsification stability and stickiness are good; and it is not preferable when a is 60 because stickiness arises while there is no significant effect on the emulsification stability. These results indicate that the preferable range of a is 5–50. Similar test results were obtained for values of b.

Table 4 shows the results of testing the emulsification stability and stickiness with various values of m and fixed values of n=10 and a=b=20 in the basic recipe shown in Table 2.

TABLE 4

| | | Comparative example 5 | Example 5 | Example 6 | Example 7 | Example 8 | Example 9 | Example 10 | Example 11 | Comparative example 8 |
|---|---|---|---|---|---|---|---|---|---|---|
| Polyether | m | 30 | 50 | 120 | 150 | 220 | 400 | 800 | 1000 | 2000 |
| modified | n | 10 | 10 | 10 | 10 | 10 | 10 | 10 | 10 | 10 |
| silicone | a | 20 | 20 | 20 | 20 | 20 | 20 | 20 | 20 | 20 |
| (the general formula (2)) | b | 20 | 20 | 20 | 20 | 20 | 20 | 20 | 20 | 20 |
| Emulsification stability | | x | ○ | ○ | ⊚ | ⊚ | ⊚ | ⊚ | ⊚ | ⊚ |
| Stickiness | | ○ | ○ | ○ | ○ | ○ | ○ | ○ | ○ | Δ |

Table 4 indicates the following: the emulsification stability is significantly poor when m is 30 and it is improved when m is 50 while the high temperature stability is somewhat poor; when m is 200 or larger, the emulsification stability, including the high temperature stability, is significantly improved; it is not preferable to increase m above 1,000 because then stickiness arises although the emulsification stability is guaranteed; therefore, the preferable range of m is 50–1,000 and the more preferable range is 150–1,000.

Table 5 shows the results of testing the emulsification stability and stickiness with various values of n and fixed values of m=400, n=10 and b=24 in the basic recipe shown in Table 2.

TABLE 5

|  |  | Comparative example 7 | Example 12 | Example 13 | Example 14 | Example 15 | Example 16 | Comparative example 8 |
|---|---|---|---|---|---|---|---|---|
| Polyether | m | 400 | 400 | 400 | 400 | 400 | 400 | 400 |
| modified | n | 0 | 1 | 3 | 10 | 30 | 40 | 50 |
| silicone | a | 20 | 20 | 20 | 20 | 20 | 20 | 20 |
| (the general formula (2)) | b | 20 | 20 | 20 | 20 | 20 | 20 | 20 |
| Emulsification stability |  | x | ○ | ⊚ | ⊚ | ⊚ | ⊚ | ⊚ |
| Stickiness |  | ○ | ○ | ○ | ○ | ○ | Δ | x |

Table 5 indicates the following: when n is 0, there is hardly any emulsification stabilizing effect; when n is 1, there is a noticeable emulsification stabilizing effect; when n is 3 or more, there is a distinctive emulsification stabilizing effect; however, when n is over 40, stickiness tends to arise; therefore, the preferable range of n is 1–40 and the more preferable range is 3–30.

Emulsified hair cosmetics of the following examples and comparative examples were evaluated for their application ease (spreadability on the hair, stickiness, smoothness), gloss and split end mending effect. The evaluation results are shown in Table 6.

EXAMPLE 17
A/O type hair cream (treatment type)

| | | (wt %) |
|---|---|---|
| (1) | Dimethyl polysiloxane (n = 3,000 in the general formula (2)) | 5 |
| (2) | Light type liquid isoparaffin | 30 |
| (3) | Polyether modified silicone (50% solution of the general formula (18) with m = 400, n = 10, a = 24 and b = 24 in isoparaffin) | 15 |
| (4) | Ethanol | 30 |
| (5) | Ion exchanged water | 19 |
| (6) | Perfume | Appropriate amount |
| (7) | Paraben | Appropriate amount |
| (8) | Antioxidant | Appropriate amount |
| (9) | Sodium glutamate | 1 |

(Preparation method)

A mixture of the components (4)–(9) was added to a mixture of the components (1), (2) and (3) using a disper for agitation to obtain an A/O type hair cream.

EXAMPLE 18
A/O type hair cream (treatment type)

| | | (wt %) |
|---|---|---|
| (1) | Decamethylcyclopentasiloxane | 15 |
| (2) | Amino modified polymer silicone ($R^a$ and $R^b$ are methyl groups, $R^c$ is $-(CH_2)_3N(CH_3)(CH_2)_2N(CH_3)_2$, x = 10,000 and y = 5 in the general formula (3)) | 10 |
| (3) | Polyether modified silicone (50% solution of the general formula (18) with m = 500, n = 20, a = 20 and b = 20 in Isoparaffin) | 15 |
| (4) | Ethanol | 40 |
| (5) | Ion exchanged water | 3.6 |
| (6) | Hyaluronic acid | 0.1 |
| (7) | Phosphatidyl choline | 0.1 |

-continued

EXAMPLE 18
A/O type hair cream (treatment type)

| | | (wt %) |
|---|---|---|
| (8) | Hydrolyzed collagen | 0.1 |
| (9) | 2-hydroxy-4-methoxybenzophenone | 0.1 |
| (10) | Perfume | Appropriate amount |
| (11) | Polyethylene glycol (molecular weight 6,000) | 1 |

(Preparation method)

The component (2) was dissolved in the component (1) and then mixed with the component (3). This oil phase was agitated with a homomixer at room temperature while a solution prepared by mixing the components (4)–(11) was added to obtain an A/O type hair cream.

COMPARATIVE EXAMPLE 9
A/O type hair cream (treatment type)

| | | (wt %) |
|---|---|---|
| (1) | Isoparaffin | 15.0 |
| (2) | Dimethyl polysiloxane (n = 1,000 in the general formula (2)) | 10.0 |
| (3) | Diglyceryl diisostearate | 2 |
| (4) | Dextrine fatty acid ester | 1.5 |
| (5) | Ion exchanged water | 67 |
| (6) | Glycerine | 4.0 |
| (7) | Polyethylene glycol 6000 | 0.5 |

(Preparation method)

The components (1)–(4) were heated up to 70° C. and mixed to prepare the oil phase. A mixture of the components (5)–(7) was then added to the oil phase using a disper for agitation to obtain an A/O type hair cream.

COMPARATIVE EXAMPLE 10
A/O type hair cream (styling type)

| | | (wt %) |
|---|---|---|
| (1) | Isoparaffin | 15 |
| (2) | Amino modified polymer silicone $R^a$ and $R^b$ are methyl groups, $R^c$ is $-(CH_2)_3N(CH_3)(CH_2)_2N(CH_3)_2$, x = 10,000 and y − 5 in the general formula (3)) | 10 |
| (3) | Diglyceryl diisostearate | 2 |
| (4) | Dextrine fatty acid ester | 1.5 |
| (5) | Hectorite treated withe | 1.5 |

-continued

COMPARATIVE EXAMPLE 10
A/O type hair cream (styling type)

|     |                                                      | (wt %) |
| --- | ---------------------------------------------------- | ------ |
| (6) | dimethylstearylammonium chlorid Ion exchanged water  | 55.5   |
| (7) | Vinylpyrolidone/dimethylaminoethyl methacrylate copolyme | 10  |
| (8) | Glycerine                                            | 4      |
| (9) | Polyethylene glycol 6000                             | 0.5    |

(Preparation method)

The components (1)–(5) were heated up to 70° C. and mixed to prepare the oil phase. A mixture of the components (6)–(9) was then added to the oil phase using a disper for agitation to obtain an A/O type hair cream.

The emulsified hair cosmetics of Examples 17 and 18 and Comparative examples 9 and 10 were evaluated using the following method. The results are shown in Table 6.

The evaluation method is described below.

[Evaluation method]

30 cm/5 g of Japanese female hair with split ends was bundled and, after shampooing, approximately 5 g of the emulsified hair cosmetics of the examples and comparative examples was directly applied to it, followed by light rinsing. A hair drier with a brush was then used to brush it. The following items were checked immediately following and two hours following the completion of the brushing.

"Application ease" (spreadability on the hair, stickiness and smoothness):

⊚: Very good tactile sense in general.
◯: Good tactile sense in general.
Δ: Not very good tactile sense in general.
X: Very poor tactile sense in general.

"Gloss"

⊚: Glossy in general.
◯: Glossy.
Δ: Somewhat glossy.
x: No gloss.

"Split ends mending effect"

The evaluation was based on the level of detachment of split ends after brushing 10 times.

⊚: Split ends are adhered and not detached.
◯: Split ends are adhered but a small portion is detached.
Δ: Most adhered split ends are detached.
X: All the adhered split ends are detached.

The results shown in Table 6 indicate that the emulsified hair cosmetics of the present invention are superior in terms of the split ends mending effect, have a good application ease and are superior in terms of lasting gloss.

Other examples of the present invention are shown below.

EXAMPLE 19
A/O type hair cream (styling type)

|     |                                                      | (wt %) |
| --- | ---------------------------------------------------- | ------ |
| (1) | Octamethylcyclotetrasiloxane                         | 15     |
| (2) | Dimethyl polysiloxane (n = 1,000 in the general formula (2)) | 15 |
| (3) | Ion exchanged water                                  | 24.9   |
| (4) | Ethanol                                              | 10     |
| (5) | Perfume                                              | Appropriate amount |
| (6) | 2-hydroxy-4-methoxybenzophenone                      | 0.1    |
| (7) | Polyether modified silicone (50% solution of the general formula (18) with m = 300, n = 20, a = 15 and b = 15 in isoparaffin) | 30 |
| (8) | Betain modified dialkylamino acrylate copolymer (Product name: Yukaformer AM75R205S from Mitsubishi Chemical Industry, Co. Ltd.) | 5 |

(Preparation method)

While a mixture prepared by dissolving the component (2) in the component (1) was agitated with a homomixer at room temperature, a mixture of the components (3)–(8) was added to it to obtain an A/O type hair cream.

EXAMPLE 20
A/O type treatment lotion

|     |                                                      | (wt %) |
| --- | ---------------------------------------------------- | ------ |
| (1) | Dimethyl polysiloxane 6cs                            | 20     |
| (2) | Amino modified polymer silicone $R^a$ and $R^b$ are methyl groups, $R^c$ is $-(CH_2)_3N(CH_3)(CH_2)N(CH_3)C=O(C_2H_5)$, x = 15,000 and y = 4 in the general formula (3)) | 10 |
| (3) | Ion exchanged water                                  | 29.9   |
| (4) | Ethanol                                              | 30     |
| (5) | Perfume                                              | Appropriate amount |
| (6) | 2-hydroxy-4-methoxybenzophenone                      | 0.1    |
| (7) | Polyether modified silicone (50% solution of the general formula (18) with m = 400, n = 10, a = 24 and b = 24 in isoparaffin) | 8 |
| (8) | Egg yolk lecithin                                    | 0.5    |

TABLE 6

|  | Split ends mending effect | | tactile sense | | Gloss | |
| --- | --- | --- | --- | --- | --- | --- |
|  | Immediately | Two hours following | Immediately | Two hours following | Immediately | Two hours following |
| Example 17 | ⊚ | ⊚ | ⊚ | ⊚ | ⊚ | ⊚ |
| Example 18 | ⊚ | ⊚ | ⊚ | ⊚ | ⊚ | ⊚ |
| Comparative example 9 | Δ | x | Δ | Δ | Δ | x |
| Comparative example 10 | ◯ | Δ | ◯ | ◯ | ◯ | Δ |

17

-continued

EXAMPLE 20
A/O type treatment lotion

| | (wt %) |
|---|---|
| (9) Egg white | 0.5 |
| (10) Vinylpyrolidone dimethylaminomethyl methacrylate copolymer | 1 |

(Preparation method)

While a mixture prepared by dissolving the component (2) in the component (1) was agitated with a homomixer at room temperature, a mixture of the components (3)–(10) was added to it to obtain an W/O type treatment lotion.

EXAMPLE 21
Hair spray (treatment type)

| | (wt %) |
|---|---|
| (1) Isoparaffin | 10 |
| (2) Amino modified polymer silicone $R^a$ is methyl group, $R^b$ is a hydroxyl group and $R^C$ is $-(CH_2)_3N^+(CH_3)_3Cl^-$, x = 18,000 and y = 2 in the general formula (3)) | 5 |
| (3) Amino modified polymer silicone $R^a$ and $R^b$ are methyl groups, $R^C$ is $-(CH_2)_3N(CH_3)_2$, x = 8,000 and y = 10 in the general formula (3)) | 5 |
| (4) Ion exchanged water | 13 |
| (5) Ethanol | 23.9 |
| (6) Perfume | Appropriate amount |
| (7) Octylmethoxy cinnamate | 0.1 |
| (8) Polyether modified silicone (50% solution of the general formula (18) with m = 400, n = 10, a = 25 and b = 25 in isoparaffin) | 3 |
| (9) Liquefied petroleum gas | 40 |

(Preparation method)

While a mixture prepared by dissolving the component (2) and the component (3) in the component (1) was agitated with a homomixer at room temperature, a mixture of the components (4)–(8) was added to it to obtain an A/O type hair cream. After this cream was put into an aerosol container and a valve was installed, the component (9) was introduced to obtain a hair spray.

EXAMPLE 22
A/O type hair cream

| | (wt %) |
|---|---|
| (1) Octamethylcyclotetrasiloxane | 15 |
| (2) Organic silicone resin with an average component unit represented by a general formula $R_nSiO_{(4-n)\ 2}$ | 6.0 |
| (3) Ion exchanged water | 24.9 |
| (4) Ethanol | 15 |
| (5) Perfume | Appropriate amount |
| (6) 2-hydroxy-4-methoxybenzophenone | 0.1 |
| (7) Polyether modified silicone (50% solution of the general formula (18) with m = 250, n = 25, a = 18 and b = 18 in isoparaffin) | 30 |

(Preparation method)

While a mixture prepared by dissolving the component (2) in the component (1) was agitated with a homomixer at room temperature, a mixture of the components (3)–(7) was added to it to obtain an A/O type hair cream.

What is claimed is:

1. A lower alcohol-in-oil stable emulsified hair cosmetic without a surfactant, comprising:

(A) one or more silicone derivative;
   (B) one or more polyether modified silicones represented by the following general formula (1):

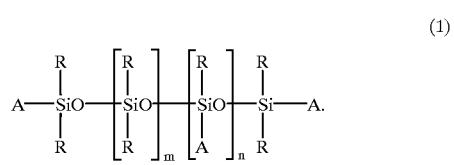

(1)

and (C) a lower alcohol;

wherein, A denotes a member selected from the group consisting of methyl group, a phenyl group and a polyoxyalkylene group represented by the general formula $-C_3H_6O(C_2H_4O)_a(C_3H_6O)_bR'$ (where R' denotes a member selected from the group consisting of a hydrogen atom, acyl group and alkyl group with a carbon number of 1–4, a denotes an integer 5–50 and b denotes an integer 5–50); at least one of the three A's is a polyoxyalkylene group; R denotes a methyl group or phenyl group; m denotes an integer 50–1,000; n denotes an integer 1–40; the polyether modified silicone contains 40 wt % or more of polyoxyalkyene groups in its molecules; and the molecular weight of the polyether modified silicone is 30,000 or more.

2. The lower alcohol-in-oil stable emulsified hair cosmetic of claim 1, wherein said silicone derivative is a high molecular weight dimethylpolysiloxane represented by the following general formula (2):

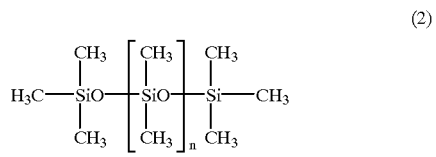

(2)

wherein, n denotes an integer 3,000–20,000.

3. The lower alcohol-in-oil stable emulsified hair cosmetic of claim 1, wherein said silicone derivative is an amino modified or ammonium modified silicone represented by the following general formula (3):

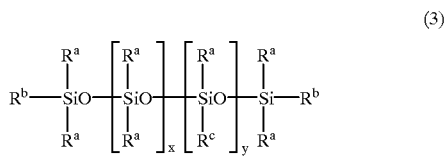

(3)

wherein, $R^a$ denotes a methyl group or a phenyl group; $R^b$ denotes the same as $R^c$ or a methyl group or hydroxyl group; $R^c$ denotes a substitutional group containing an amino group or ammonium group represented by the formula $R^dZ$ {$R^d$ denotes a divalent alkylene group containing 3–6 carbon atoms, Z denotes a monovalent group selected from among $-NR^e_2$, $-N^+R^e_3A^-$, $-NR^e(CH_2)_nNR^e_n$, $-NR^e(CH_2)_nN^+R^e_3A$ and $-NR^e(CH_2)_nN(R^e)CO(R^F)$ ($R^e$ denotes hydrogen or an alkyl group containing 1–4 carbon atoms, $R^F$ denotes an alkyl group containing 1–4 carbon atoms, A denotes a chlorine atom, bromine atom or iodine atom, and n denotes an integer 2–6.)}; x and y each denotes a positive integer; and x+y denotes an integer 3,000–20,000 and y/x is in the range of 1/500–1/10,000.

4. The lower alcohol-in-oil stable emulsified hair cosmetic of claim 1, wherein the content of said lower alcohol is 30–80 wt % of the total emulsified hair cosmetic.

5. The lower alcohol-in-oil stable emulsified hair cosmetic of claim 2, wherein the content of said lower alcohol is 30–80 wt % of the total emulsified hair cosmetic.

6. The lower alcohol-in-oil stable emulsified hair cosmetic of claim 3, wherein the content of said lower alcohol is 30–80 wt % of the total emulsified hair cosmetic.

* * * * *